United States Patent
Sakata et al.

(10) Patent No.: US 11,156,581 B2
(45) Date of Patent: Oct. 26, 2021

(54) BIOSENSOR

(71) Applicant: THE UNIVERSITY OF TOKYO, Tokyo (JP)

(72) Inventors: Toshiya Sakata, Tokyo (JP); Taira Kajisa, Tokyo (JP); Yuya Miyazawa, Tokyo (JP); Yuta Uematsu, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 14/907,934

(22) PCT Filed: Aug. 7, 2014

(86) PCT No.: PCT/JP2014/070823
§ 371 (c)(1),
(2) Date: Jan. 27, 2016

(87) PCT Pub. No.: WO2015/020131
PCT Pub. Date: Feb. 12, 2015

(65) Prior Publication Data
US 2016/0169835 A1    Jun. 16, 2016

(30) Foreign Application Priority Data

Aug. 8, 2013   (JP) .............................. JP2013-165086

(51) Int. Cl.
*G01N 27/414*    (2006.01)
*G01N 27/327*    (2006.01)
(Continued)

(52) U.S. Cl.
CPC ....... *G01N 27/4145* (2013.01); *G01N 27/327* (2013.01); *G01N 27/414* (2013.01);
(Continued)

(58) Field of Classification Search
CPC ........... H01L 2924/13072; H01L 2924/13073; G01N 27/414
See application file for complete search history.

(56) References Cited

U.S. PATENT DOCUMENTS 4,437,969 A * 3/1984 Covington ........... G01N 27/414
204/403.01
4,446,474 A * 5/1984 Mizusaki ............. G01N 27/414
204/419
(Continued)

FOREIGN PATENT DOCUMENTS

DE    4338732 A1    5/1995
EP    2518482 A1    10/2012
(Continued)

OTHER PUBLICATIONS

Reinhoudtetal. (Advanced Materials, 2, 23-32, 1990) (Year: 1990).*
(Continued)

*Primary Examiner* — Alexander S Noguerola
(74) *Attorney, Agent, or Firm* — Myers Bigel, P.A.

(57) ABSTRACT

A biosensor that can perform analysis based on a sample noninvasively collected from a human body is provided. The biosensor comprises an identification substance (38) that binds to a substance to be detected (40), and an electrode (16) charged with a charge of the identification substance (38), comprises an inhibitor (39) that inhibits a substance not to be detected (42) from attaching to at least one of the identification substance (38) and the electrode (16), and detects a change in a charge density of the electrode (16) caused by binding of the substance to be detected (40) to the identification substance (38).

11 Claims, 10 Drawing Sheets

(51) Int. Cl.
*G01N 27/416* (2006.01)
*G01N 33/53* (2006.01)

(52) U.S. Cl.
CPC ..... *G01N 27/4161* (2013.01); *G01N 33/5308* (2013.01); *G01N 2400/00* (2013.01); *H01L 2924/13072* (2013.01)

(56) References Cited

U.S. PATENT DOCUMENTS

| | | | |
|---|---|---|---|
| 6,063,637 A * | 5/2000 | Arnold | A61B 5/14539 422/82.01 |
| 7,368,085 B2 | 5/2008 | Gu et al. | |
| 7,994,593 B2 * | 8/2011 | Takulapalli | G01N 27/4145 257/414 |
| 8,344,733 B2 | 1/2013 | Nakamura et al. | |
| 8,394,247 B2 | 3/2013 | Kamahori et al. | |
| 8,668,871 B2 | 3/2014 | Matsumoto et al. | |
| 8,669,124 B2 | 3/2014 | Merz | |
| 2003/0186773 A1 | 10/2003 | Iwazaki et al. | |
| 2009/0014757 A1 | 1/2009 | Takulapalli et al. | |
| 2009/0071826 A1 * | 3/2009 | Kamahori | G01N 27/3335 204/418 |
| 2010/0137143 A1 * | 6/2010 | Rothberg | C12Q 1/6874 506/2 |
| 2012/0088990 A1 * | 4/2012 | Bunge | A61B 5/14503 600/309 |
| 2012/0244037 A1 | 9/2012 | Matsumoto et al. | |
| 2012/0247976 A1 * | 10/2012 | Yan | G01N 27/4145 205/777.5 |

FOREIGN PATENT DOCUMENTS

| | | |
|---|---|---|
| JP | 08-338798 | 12/1996 |
| JP | 2000510233 A | 8/2000 |
| JP | 2003287062 A | 10/2003 |
| JP | 2008-134255 | 6/2008 |
| JP | 2008527392 A | 7/2008 |
| JP | 2010-107496 A | 5/2010 |
| JP | 2010-164513 | 7/2010 |
| JP | 2010-243301 | 10/2010 |
| JP | 2012026839 A | 2/2012 |
| JP | 2012053061 A | 3/2012 |
| JP | 2012-070907 A | 4/2012 |
| JP | 2013-027623 A | 2/2013 |
| TW | 201011290 A | 3/2010 |
| WO | WO 97/41425 A1 | 11/1997 |
| WO | WO 2005/015193 A1 | 2/2005 |
| WO | WO 2006/078224 A1 | 7/2006 |

OTHER PUBLICATIONS

Moussy et al. (Anal. Chem. 65, 2072-2077) (Year: 1993).*
Harrison et al. (Anal. Chem. 60, 2002-2007) (Year: 1988).*
EPO computer-generated English language translation of the Description section DE 4338732 A1, downloaded Jun. 19, 2021, patent published May 18, 1995 (Year: 1995).*
Uematsu et al. "Development of glucose transistor for highly sensitive detection of glucose in biogenic fluid", *Japan Society of Applied Physics and Related Societies* p. 12-174, 28p-G17-4 (Mar. 28, 2013) (2 pages in English).
Office Action corresponding to Japanese Application No. 2013-165086 dated Dec. 12, 2013.
Office Action corresponding to Japanese Application No. 2013-095988 dated Jul. 2, 2013.
Office Action corresponding to Taiwanese Application No. 10321731260 dated Dec. 11, 2014.
Springsteen et al. "A detailed examination of boronic acid-diol complexation", *Tetrahedron* 58:5291-5300 (2002).
Extended European Search Report corresponding to European Application No. 14835100.0 dated Feb. 22, 2017.
Matsumoto et al. "Chemical-to-Electrical-Signal Transduction Synchronized with Smart Gel Volume Phase Transition", Advanced Materials 21:4372-4378 (2009).
Matsumoto et al. "Glucose-sensitive field effect transistor using totally syntheitc compounds", Journal of Solid State Electrochemistry 13:165-170 (2009).
U.S. Appl. No. 14/787,414, filed Oct. 27, 2015; Office Action dated Jul. 6, 2018.
Maeda et al. "Preparation of alpha-mannoside hydrogel and electrical detection of saccharide-protein interactions using the smart gel-modified gate field effect transistor", Nanosoale Research Letters 7(1):108 (2012) 8 pages.
U.S. Appl. No. 14/787,414, filed Oct. 27, 2015; Office Action dated Mar. 12, 2018.
U.S. Appl. No. 14/787,414, filed Oct. 27, 2015; Office Action dated Sep. 18, 2017.
U.S. Appl. No. 14/787,414, flied Oct. 27, 2015; Office Action dated Oct. 10, 2019.
T. Goda, et al. "Detection of Microenvironmental Changes Induced by Protein Adsorption onto Self-Assembled Monolayers using an Extended Gate-Field Effect Transistor", Analytical Chemistry, 82(5): p. 1803-1810, March (Year: 2010).
"Extended European Search Report corresponding to European Patent Application No. 20173841.6, dated Jun. 24, 2020".
Sallacan, Nesim, et al., "Imprinting of Nucleotide and Monosaccharide Recognition Sites in Acrylamidephenylboronic Acid—Acrylamide Copolymer Membranes Associated with Electronic Transducers", Analytical Chemistry, vol. 74, Feb. 2002, 702-712.

* cited by examiner

[Figure 1]
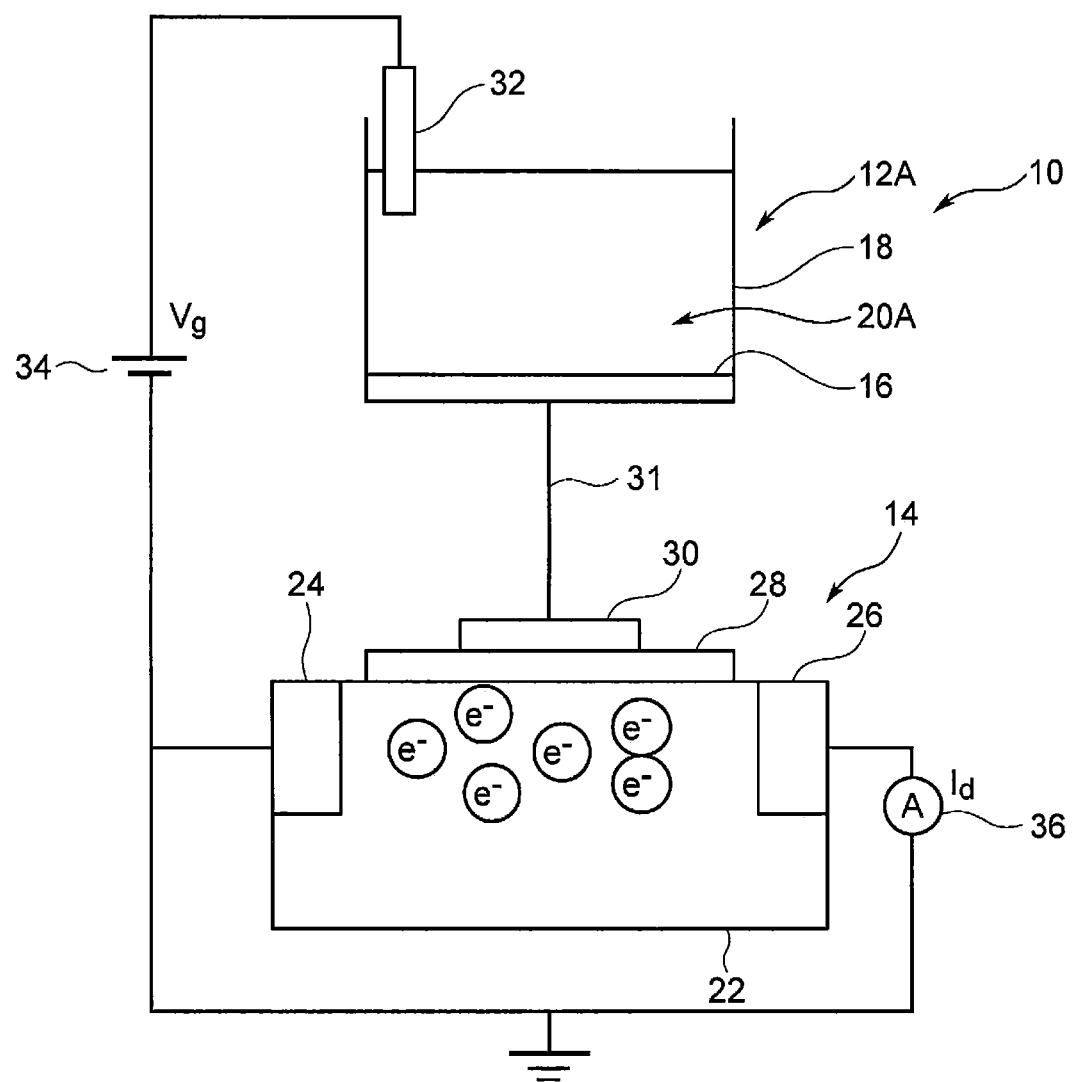

[Figure 2]
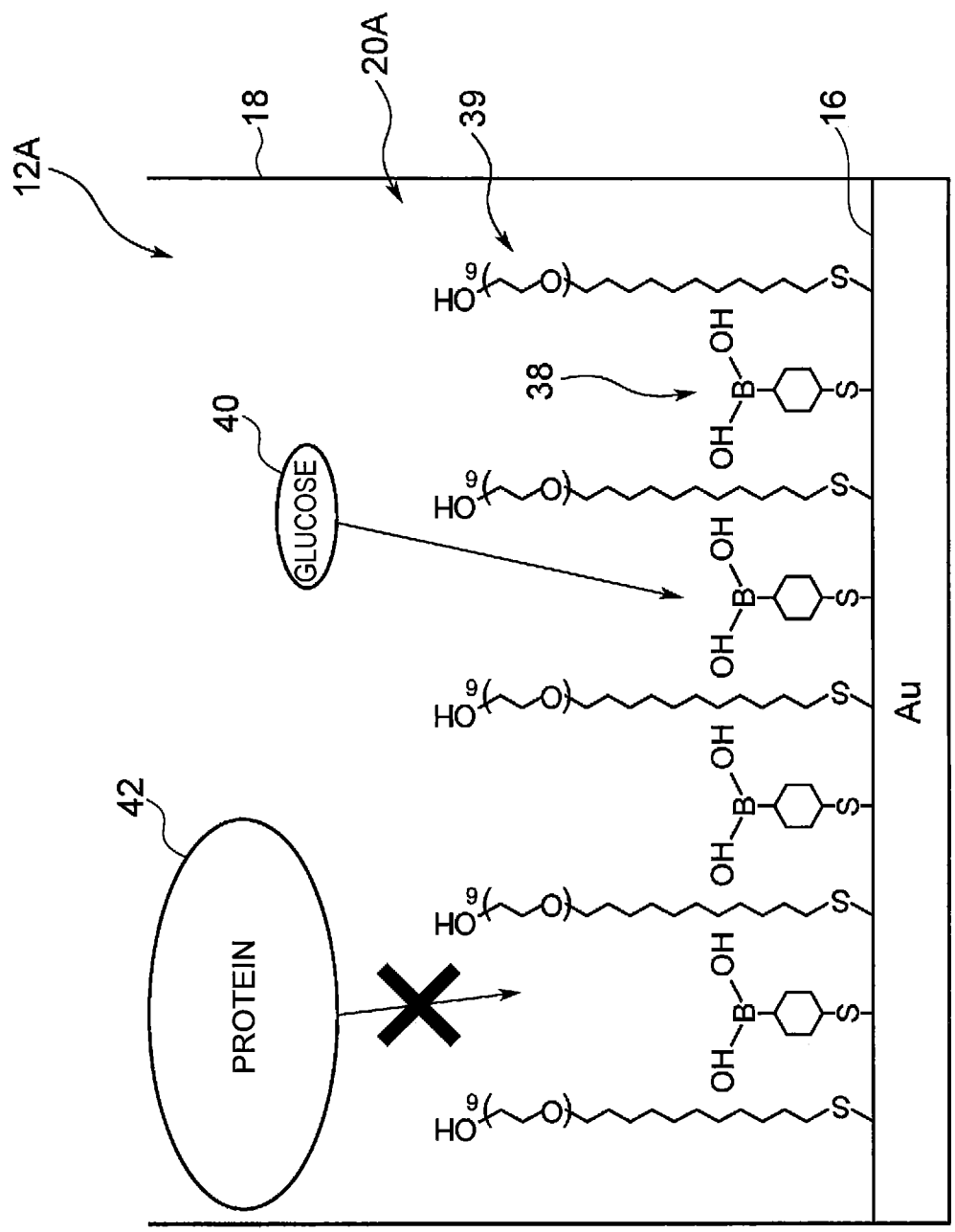

[Figure 3]
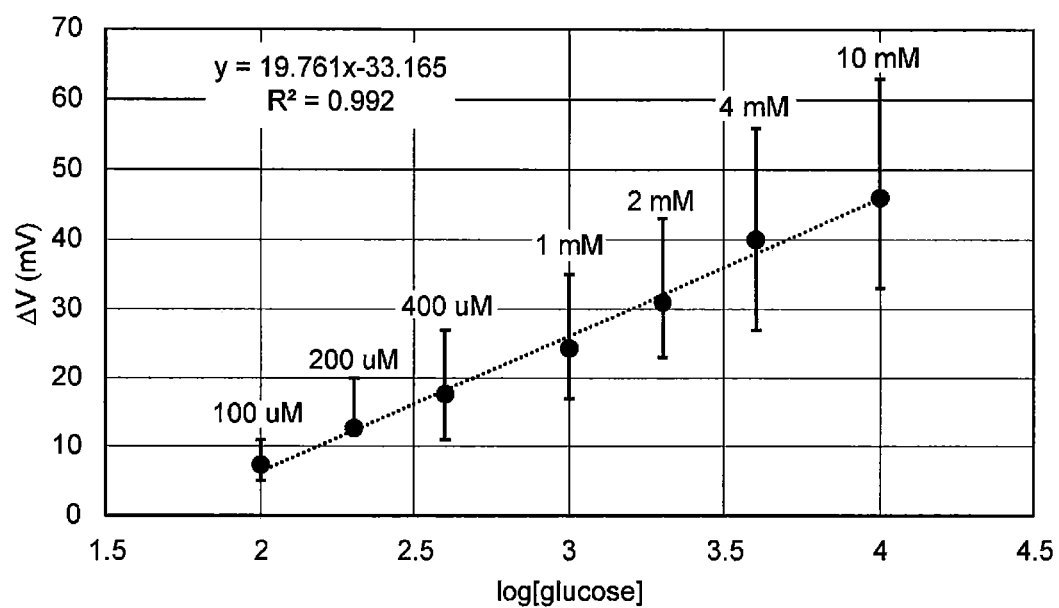

[Figure 4]
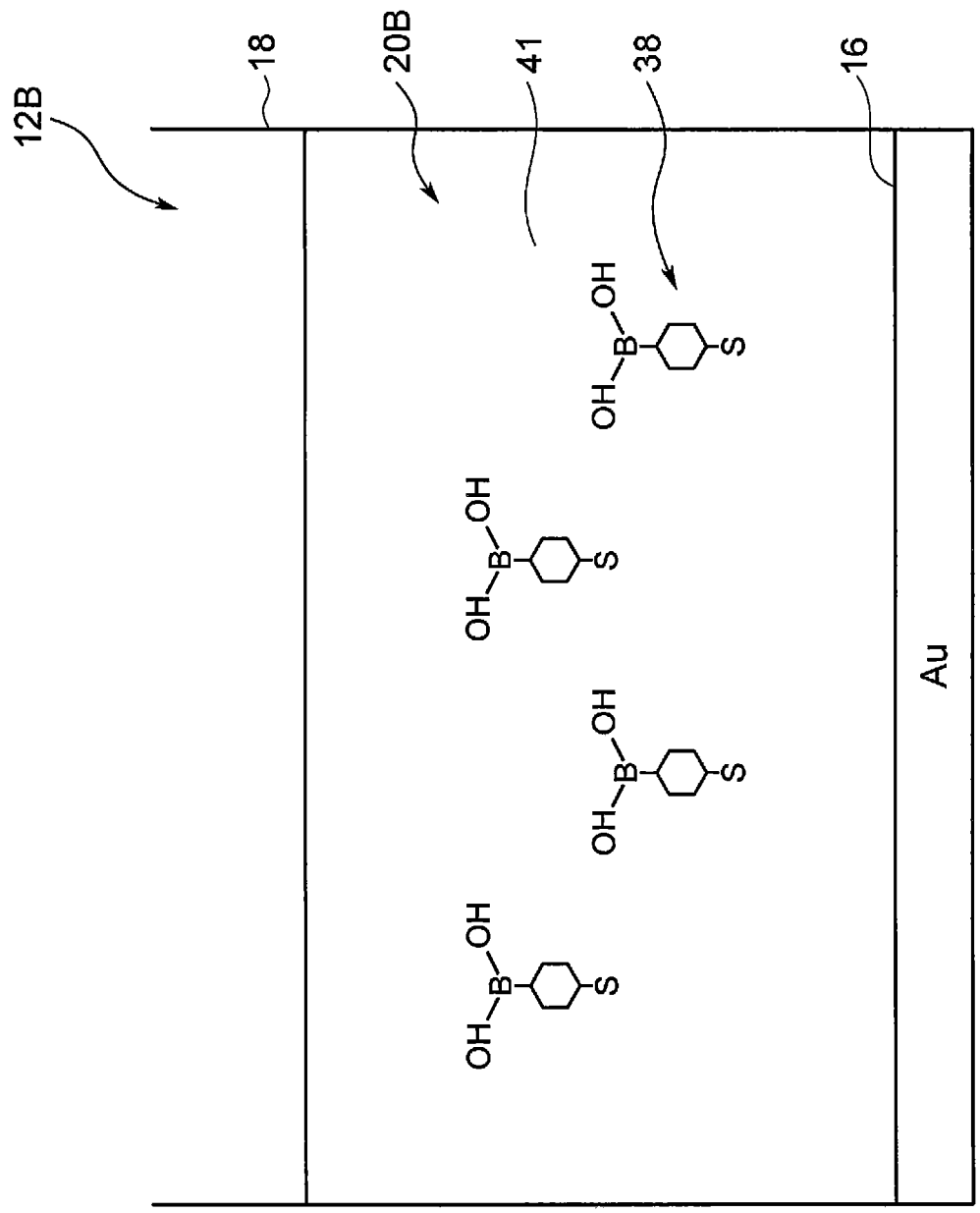

[Figure 5]
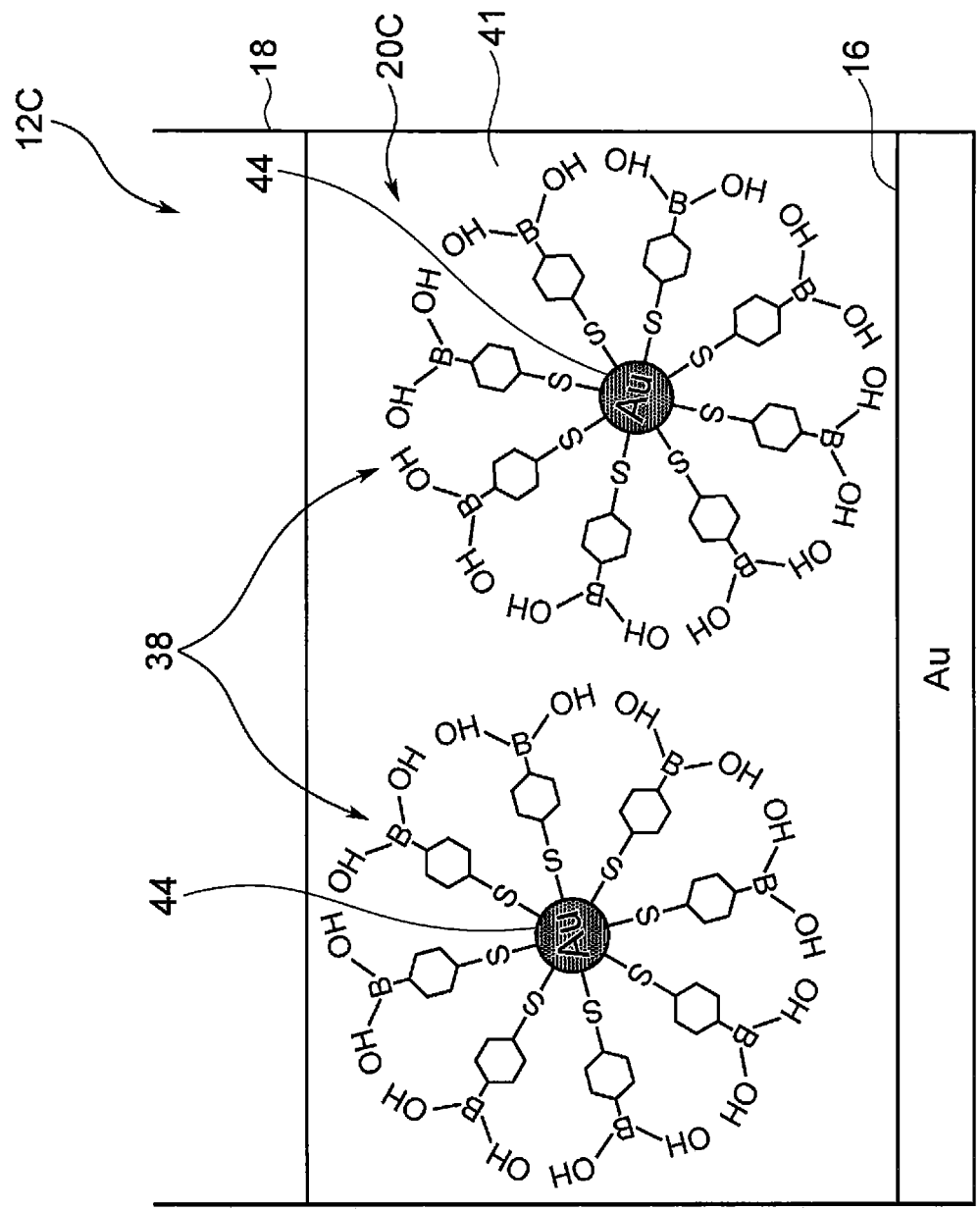

[Figure 6]
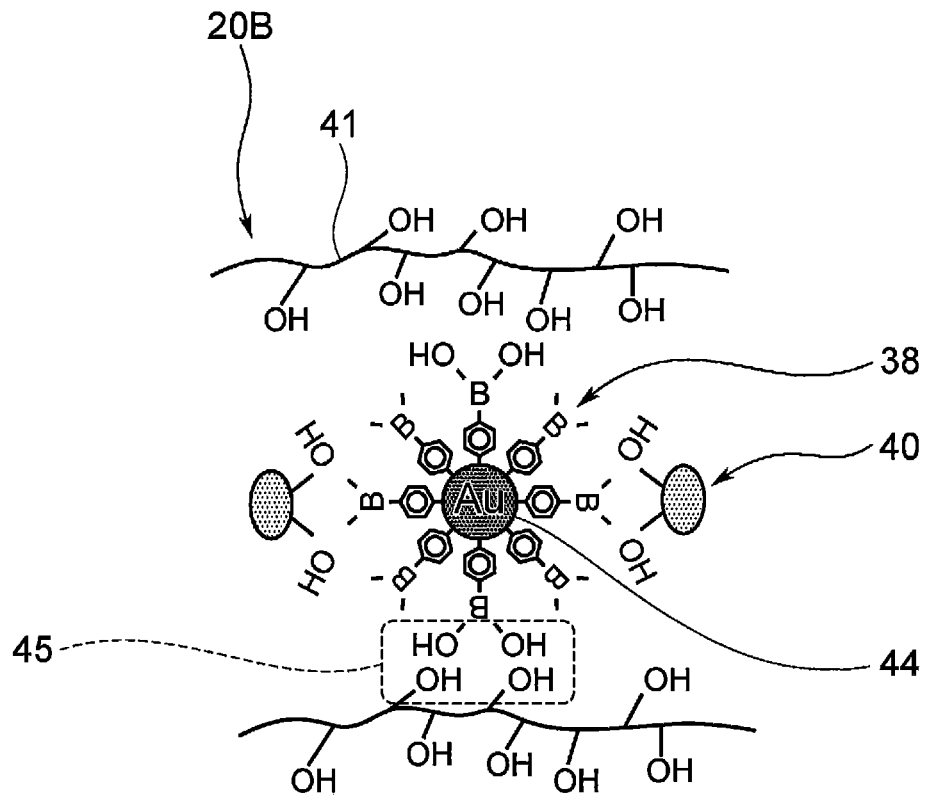
[Figure 7]
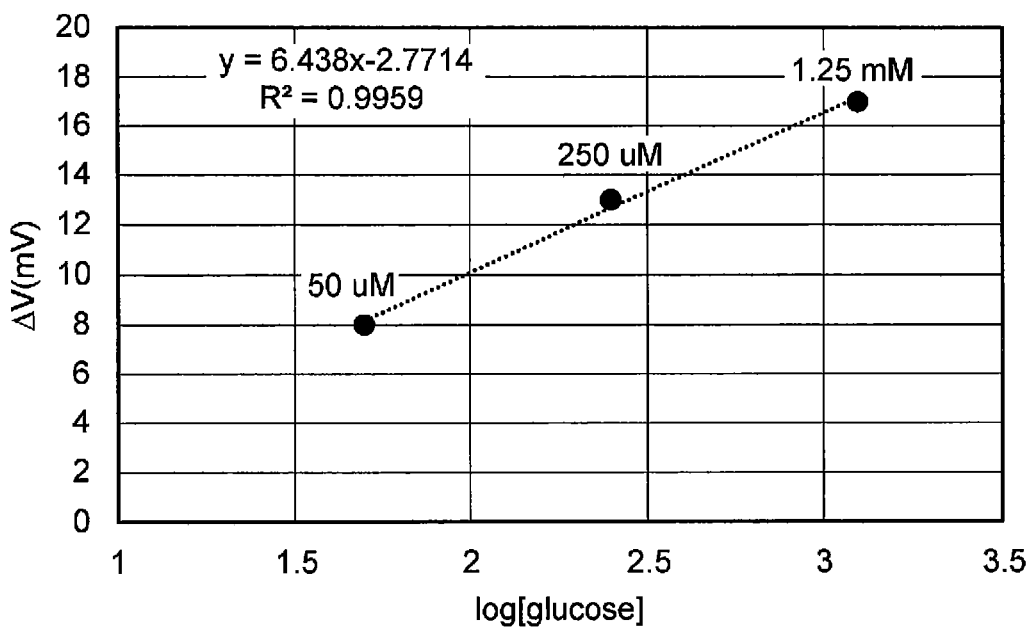

[Figure 8]
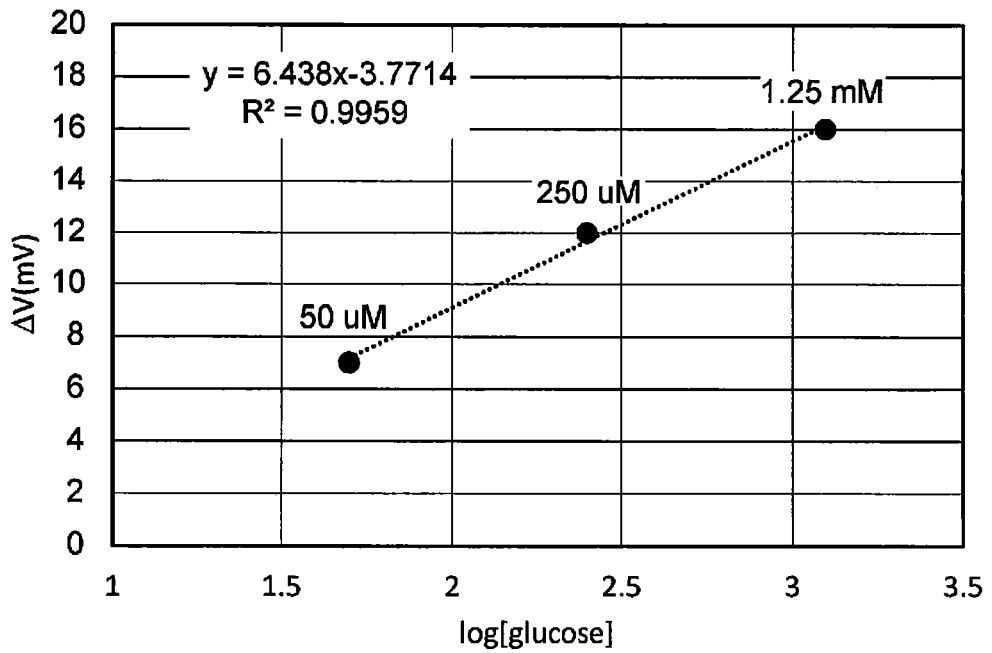
[Figure 9]
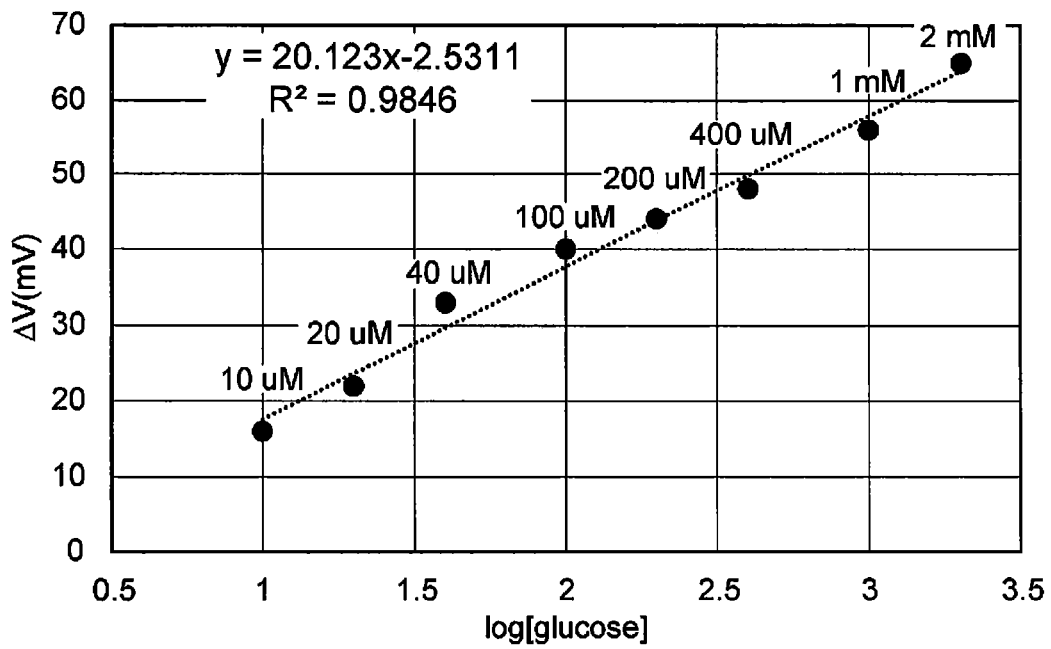

[Figure 10]
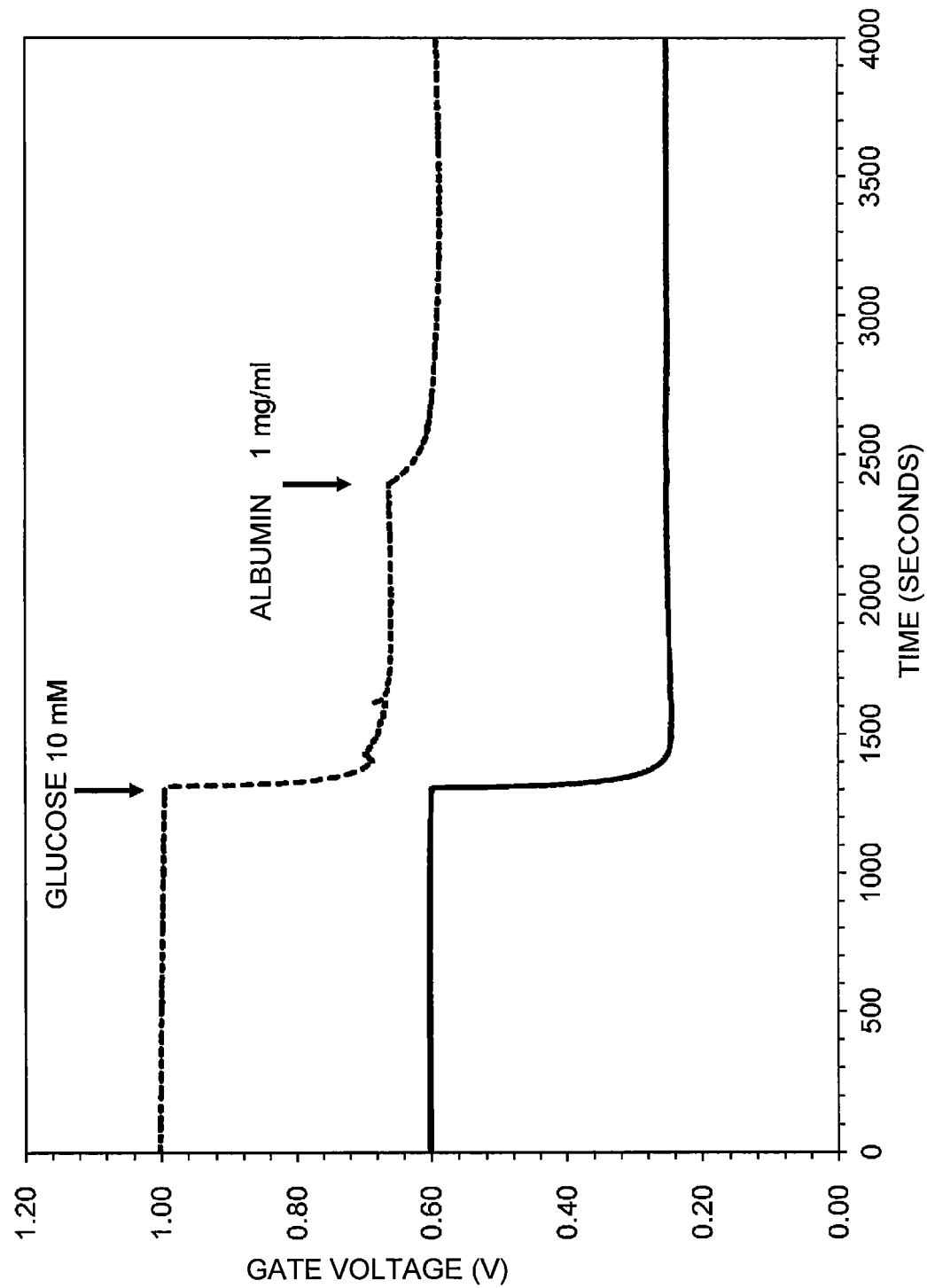

[Figure 11]
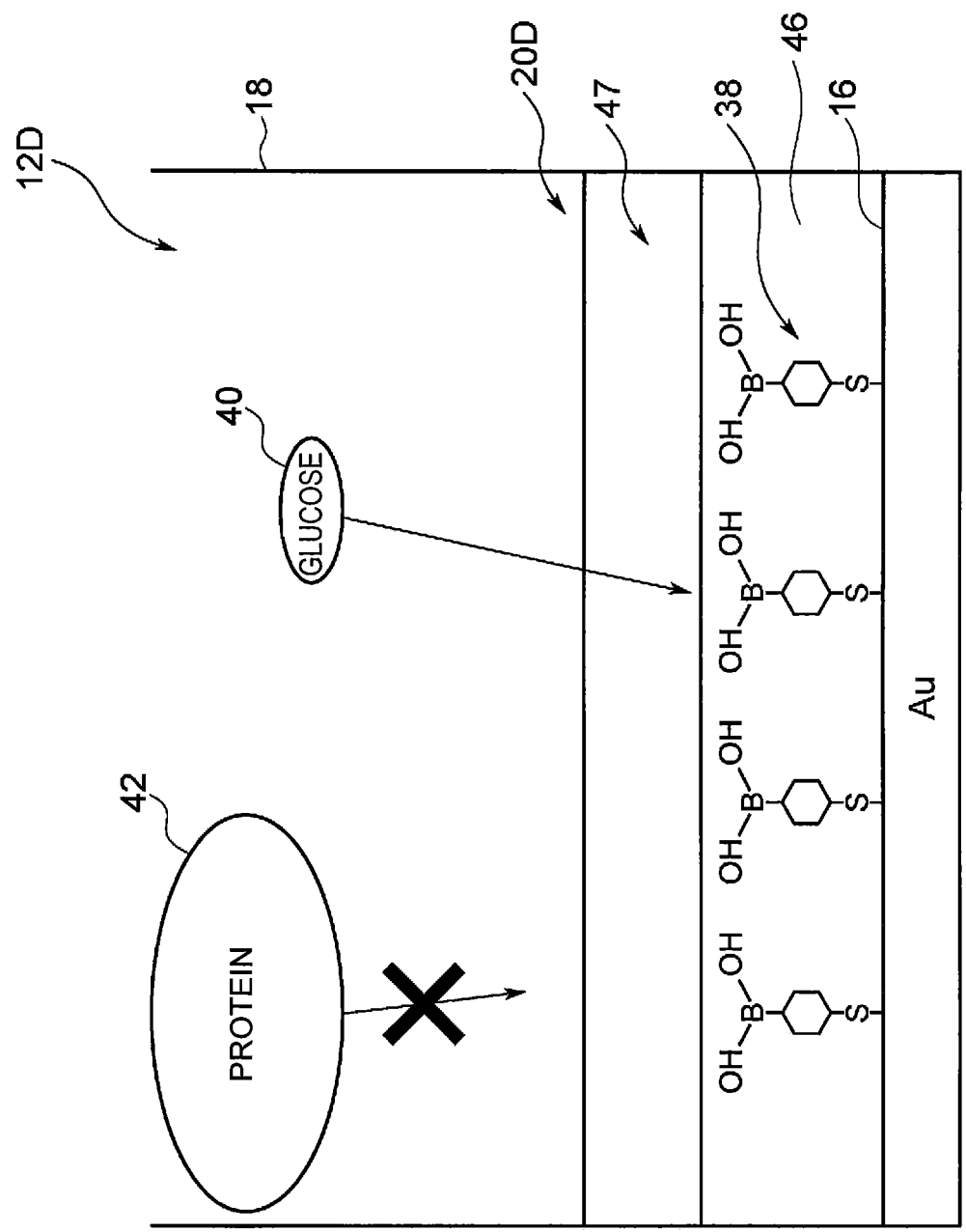

[Figure 12]
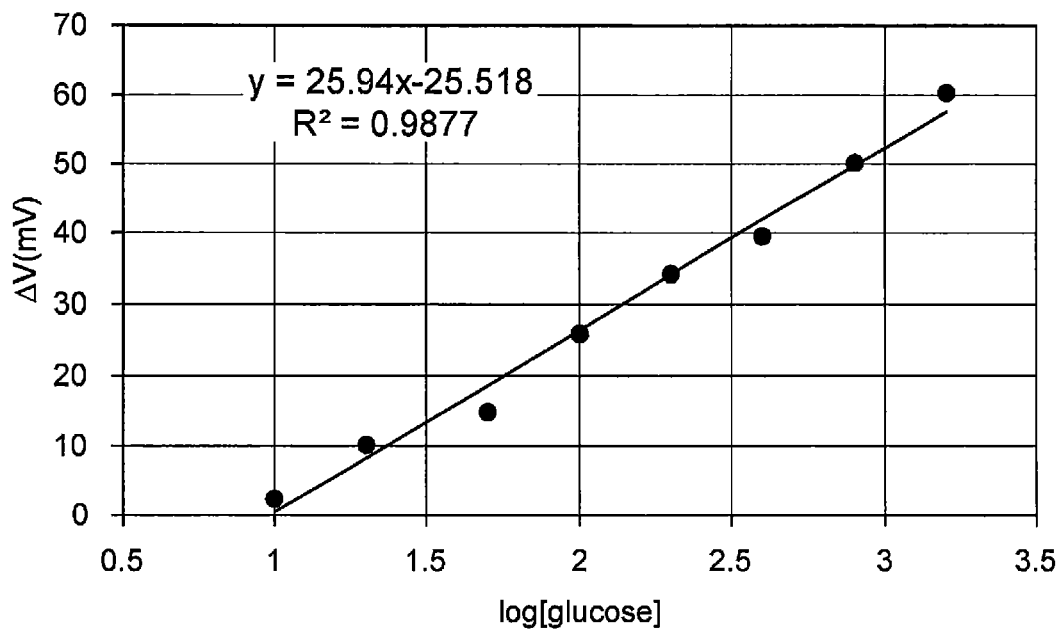

BIOSENSOR

RELATED APPLICATIONS

This application is a 35 U.S.C. § 371 national phase application of PCT Application PCT/JP2014/070823 filed Aug. 7, 2014 which claims priority to Japanese Application No. 2013-165086 filed Aug. 8, 2013. The entire content of each is incorporated herein by reference in its entirety.

TECHNICAL FIELD

The present invention relates to a biosensor.

BACKGROUND ART

In recent years, as biosensors, techniques in which living cells can be noninvasively utilized for analysis have been disclosed (for example, Patent Literature 1). Patent Literature 1 discloses a biosensor having a structure in which a detection surface that detects a change in the physical properties of a negative charge is coated with phenylboronic acid groups that bind to a sialic acid sample (a cell itself or a sugar chain derived from a cell).

CITATION LIST

Patent Literature

Patent Literature 1: Japanese Patent Laid-Open No. 2010-107496

SUMMARY OF INVENTION

Technical Problem

However, in the biosensor described in the above Patent Literature 1, cells and the like are not invaded, but it cannot be said that a human body is not invaded when cells are collected. In other words, a biosensor that can further reduce the burden on a human body, for example, a biosensor that can detect a substance to be detected, based on tears, sweat, saliva, or the like, is desired. In this connection, in addition to glucose as a substance to be detected, proteins such as albumin are contained in tears and the like, and there is a fear that the proteins as noise decrease measurement sensitivity.

Accordingly, it is an object of the present invention to provide a biosensor that can perform analysis based on a sample noninvasively collected from a human body.

Solution to Problem

A biosensor according to the present invention is a biosensor comprising an identification substance that binds to a substance to be detected, and an electrode charged with a charge of the identification substance, in which the biosensor comprises an inhibitor that inhibits a substance not to be detected from attaching to at least one of the identification substance and the electrode; the identification substance is in contact with the electrode; the inhibitor is formed of a polymer compound having a longer molecular chain than the identification substance; a self-assembled monolayer is formed on a surface of the electrode from the identification substance and the inhibitor; and the biosensor detects a change in a charge density of the electrode caused by binding of the substance to be detected to the identification substance.

In addition, a biosensor according to the present invention is a biosensor comprising an identification substance that binds to a substance to be detected, and an electrode charged with a charge of the identification substance, in which the biosensor comprises an inhibitor that inhibits a substance not to be detected from attaching to at least one of the identification substance and the electrode; the biosensor comprises a thin film provided on the electrode and formed of the identification substance, and one or two or more inhibitor layers formed on the thin film and comprising the inhibitor; and the biosensor detects a change in a charge density of the electrode caused by binding of the substance to be detected to the identification substance.

Further, a biosensor according to the present invention is a biosensor comprising an identification substance that binds to a substance to be detected, and an electrode charged with a charge of the identification substance, in which the biosensor comprises an inhibitor that inhibits a substance not to be detected from attaching to at least one of the identification substance and the electrode; the identification substance is bound to the inhibitor; and the biosensor detects a change in a charge density of the electrode caused by binding of the substance to be detected to the identification substance.

Advantageous Effect of Invention

According to the present invention, the substance not to be detected can be inhibited from binding to the identification substance or attaching to the surface of the electrode by the inhibitor, and therefore the measurement sensitivity can be further improved. Therefore, the biosensor can more reliably measure glucose concentrations based on a sample noninvasively collected from a human body.

BRIEF DESCRIPTION OF DRAWINGS

FIG. 1 is a schematic view showing the entire configuration of a biosensor according to a first embodiment.

FIG. 2 is a schematic view showing the configuration of an identification portion in the biosensor according to the first embodiment.

FIG. 3 is a graph showing the relationship between glucose concentration and gate voltage change in the biosensor according to the first embodiment.

FIG. 4 is a schematic view showing the configuration of an identification portion in a biosensor according to a second embodiment.

FIG. 5 is a schematic view showing the configuration of an identification portion in a biosensor according to a modification of the second embodiment.

FIG. 6 is a schematic view used for the explanation of the identification portion in the biosensor according to the second embodiment.

FIG. 7 is a graph showing the relationship (1) between glucose concentration and gate voltage change in a biosensor according to the second embodiment.

FIG. 8 is a graph showing the relationship (2) between glucose concentration and gate voltage change in a biosensor according to the second embodiment.

FIG. 9 is a graph showing the relationship (3) between glucose concentration and gate voltage change in a biosensor according to the second embodiment.

FIG. 10 is a graph showing the relationship (4) between glucose concentration and gate voltage change in a biosensor according to the second embodiment.

FIG. 11 is a schematic view showing the configuration of an identification portion in a biosensor according to a modification of a third embodiment.

FIG. 12 is a graph showing the relationship between glucose concentration and gate voltage change in a biosensor according to the third embodiment.

DESCRIPTION OF EMBODIMENTS

Embodiments of the present invention will be described in detail below with reference to the drawings.

1. First Embodiment (1-1) Entire Configuration

A biosensor 10 shown in FIG. 1 comprises an identification portion 12A and a field effect transistor (FET) 14 as a detection portion. The biosensor 10 identifies glucose, as a substance to be detected, contained in a sample in the identification portion 12A and converts the identified information to an electrical signal in the FET 14 to detect glucose concentration in the sample. Here, examples of the sample can include noninvasively collected samples, that is, sweat, tears, and saliva as biological fluids other than blood. In addition to glucose, proteins such as albumin as substances not to be detected are contained in these samples.

The identification portion 12A comprises an electrode 16 and a receptor 20A provided on the electrode 16. In the case of this embodiment, in the identification portion 12A, a container 18 is formed by providing a cylindrical wall portion on one side surface of the electrode 16, and an identification substance and an inhibitor are contained in the container 18. The electrode 16 can be formed of Au but can also be formed of, for example, Ag or Cu. The receptor 20A is formed of a Self-Assembled Monolayer (SAM) comprising an identification substance and an inhibitor. The SAM usually refers to an organic thin film in which at the interface between a solid and a liquid or the interface between a solid and a gas, organic molecules gather together spontaneously and spontaneously form a monolayer.

The identification substance has the function of binding to glucose contained in a sample. For the identification substance, phenylboronic acid can be used, and in addition, for example, derivatives thereof (for example, phenylboronic acid having a vinyl group), and glucose-binding proteins (GBPs) and derivatives thereof can be used. For example, phenylboronic acid produces a negative charge when binding to glucose.

The inhibitor inhibits a protein such as albumin, a substance not to be detected, from binding to phenylboronic acid or attaching to the surface of the electrode 16. In the case of this embodiment, the inhibitor is formed of a polymer compound. For the polymer compound, oligoethylene glycol having a longer molecular chain than the identification substance can be used, and in addition, for example, polyethylene glycol can also be used.

As shown in FIG. 2, one end of each of an identification substance 38 and an inhibitor 39 adsorbs on one side surface of the electrode 16 to form an SAM. In the identification substance 38 and the inhibitor 39, a thiol group (—SH) or a disulfide group (—S—S—) is introduced to form derivatives of thiols or disulfides. Such derivatives of thiols or disulfides can form a high density thin film on the surface of a metal such as Au, Ag, or Cu. For example, phenylboronic acid into which a thiol group is introduced forms a strong bond such as Au—S. The identification substance 38 binds to glucose at the other end. The inhibitor 39 specifically binds to a substance not to be detected at the other end.

The FET 14 comprises a source 24 and a drain 26 formed on a surface of a semiconductor substrate 22, and a gate insulating film 28 formed on the semiconductor substrate 22, the source 24, and the drain 26 (FIG. 1). For the FET 14, both n-MOS and p-MOS can be used. A metal electrode 30 is formed on the gate insulating film 28. The metal electrode 30 is electrically connected to the electrode 16 via wiring 31. The metal electrode 30 can be formed of Au, Ag, Cu, or the like.

The semiconductor substrate 22 may be formed of Si, Ga, As, ITO, IGZO, IZO, or the like, or an organic semiconductor, a carbon semiconductor (for example, carbon nanotubes, a graphene semiconductor, or a diamond semiconductor), or the like may be used. The gate insulating film 28 can be formed of an oxide or a nitride such as $SiO_2$, $Si_3N_4(SiN_x)$, $Ta_2O_5$, or $Al_2O_3$.

A power supply 34 and an ammeter 36 are electrically connected to the source 24 and the drain 26, and thus the drain current flowing from the source 24 to the drain 26 can be measured. When the charge density on the gate insulating film 28 changes, the magnitude of the drain current changes. In other words, in order to keep the drain current constant, it is necessary to change gate voltage with a change in charge density on the gate insulating film 28. By measuring a change in the gate voltage of the FET 14, a change in charge density on the gate insulating film 28 is electrically measured.

At this time, a reference electrode 32 may be used as shown in this figure. The reference electrode 32 is the electrode 16 that has reference potential in the FET 14, and is electrically connected to the identification substance 38 in the identification portion 12A.

(1-2) Manufacturing Method

The identification portion 12A shown in FIG. 2 can be manufactured by the following procedure. First, Cr and Au are deposited in this order on a glass substrate using a sputtering apparatus to form the electrode 16. Then, a cylindrical wall portion formed of glass is fixed on the electrode 16 with an epoxy resin followed by washing treatment using a mixed solution of sulfuric acid and hydrogen peroxide and further washing with pure water and ethanol in this order.

Then, a mixed liquid obtained by mixing an ethanol solvent comprising 1 mM oligoethylene glycol (Hydroxy-$EG_6$-undecanethiol) and an ethanol solvent comprising 1 mM 4-mercaptophenylboronic acid at a ratio of 9:1 is put in the container 18. By holding this state for a predetermined time, the oligoethylene glycol and the phenylboronic acid chemisorb on the surface of the electrode 16, and a self-assembled monolayer is formed. Finally, the mixed liquid is removed followed by washing with ethanol and pure water in this order. The identification portion 12A can be manufactured in this manner.

(1-3) Action and Effect

In the biosensor 10 formed as described above, first, a sample is added to the identification portion 12A (FIG. 2). Glucose 40 contained in the sample reaches the lower part of the receptor 20A and binds to the identification substance 38. Thus, the identification substance 38 produces a negative charge. The surface of the electrode 16 is charged with the negative charge. On the other hand, a protein 42 such as albumin contained in the sample binds to the inhibitor 39 and is inhibited from reaching the lower part of the receptor 20A, that is, the identification substance 38, or the surface of the electrode 16.

The electrode 16 is electrically connected to the metal electrode 30 of the FET 14, and therefore when the surface of the electrode 16 is charged with the negative charge, the charge density on the gate insulating film 28 changes. A change in gate voltage accompanying the change in charge density on the gate insulating film 28 of the FET 14 is measured. Thus, the biosensor 10 can detect the concentration of the glucose contained in the sample.

In this connection, the protein 42 has a negative charge and therefore increases the negative charge with which the surface of the electrode 16 is charged by binding to the identification substance 38 or attaching to the surface of the electrode 16. Thus, conventional biosensors have the problem of a significant decrease in measurement sensitivity.

In the case of this embodiment, in the biosensor 10, the protein 42 is inhibited from reaching the identification substance 38 or the surface of the electrode 16 by the inhibitor 39 contained in the receptor 20A. Thus, in the biosensor 10, the protein 42 can be inhibited from binding to the identification substance 38 or attaching to the surface of the electrode 16, and therefore the electrode 16 can be inhibited from being charged with an unnecessary negative charge. Therefore, in the biosensor 10, the measurement sensitivity can be further improved, and therefore the glucose concentration can be more reliably measured based on a sample noninvasively collected from a human body.

(1-4) Relationship Between Glucose Concentration and Gate Voltage Change

Next, a biosensor comprising the identification portion shown in FIG. 2 was manufactured by the procedure shown in the above "(1-2) Manufacturing Method." In the identification portion, phenylboronic acid was used as an identification substance, and oligoethylene glycol was used as an inhibitor. Then, a sample comprising albumin was placed in the identification portion, and further a change in the gate voltage of the field effect transistor when the glucose concentration was gradually changed was measured.

For the sample, Phosphate buffered saline (PBS) having a pH of 7.4 and comprising 4 g/L albumin was provided, and glucose was added thereto stepwise in the range of 100 µM to 10 mM to increase the glucose concentration stepwise. The results are shown in FIG. 3.

In FIG. 3, the vertical axis shows gate voltage change (mV), and the horizontal axis shows the logarithm (log) of glucose concentration. The correlation coefficient was 0.992, and the slope was 19.761, and it was confirmed that a linear relationship was seen between the logarithm of glucose concentration and the gate voltage change. In other words, it can be said that the biosensor is not influenced by the noise of the protein, and therefore the amount of gate voltage change increases correspondingly to the glucose concentration. From the above results, it was confirmed that by using a receptor formed of a monolayer comprising an identification substance and an inhibitor, an increase in negative charge due to a protein was inhibited.

2. Second Embodiment

An identification portion 12B according to a second embodiment will be described with reference to FIG. 4 in which like numerals refer to parts corresponding to those in FIG. 2. The identification portion 12B according to this embodiment is different from the identification portion according to the above first embodiment in that an identification substance 38 is not fixed to one side surface of an electrode 16.

(2-1) Configuration of Identification Portion

A receptor 20B contained in the identification portion 12B is formed of a copolymer in which the identification substance 38 binds to an inhibitor 41. In the case of this embodiment, the receptor 20B further comprises a decomposition accelerator and a crosslinking agent.

The inhibitor 41 is formed of a hydrophilic polymer. The hydrophilic polymer is a polymer having a hydrophilic functional group (a hydroxyl group or a carboxyl group) and is a hydrogel, paper, a Superabsorbent Polymer (SAP), or the like. In the case of this embodiment, a hydrogel is used for the inhibitor 41.

The hydrogel is a gel-like material in which hydrophilic polymer chains are crosslinked to hold a large amount of water and which provides excellent water absorbency. Examples of the hydrogel include polyhydroxyethyl methacrylate (Poly-HEMA, also referred to as poly2-hydroxyethyl methacrylate), polyvinylpyrrolidone (PVP), and polyvinyl alcohol (PVA). The Poly-HEMA may be a homopolymer of hydroxyethyl methacrylate (HEMA) or a copolymer with another monomer (for example, 2,3-dihydroxypropyl methacrylate or glycerol methacrylate (GMA)). The Poly-HEMA tends to have a higher water content when it is a copolymer. In addition, the PVP may be a homopolymer of N-vinyl-2-pyrrolidone (NVP) or a copolymer obtained by using NVP as a main component and adding HEMA, methyl methacrylate (MMA), or the like and a crosslinking agent for polymerization.

The paper is manufactured by gluing plant fibers or other fibers. The plant fibers are composed of cellulose, hemicellulose, or lignin. The cellulose has such a property that a large number of hydroxyl groups of the cellulose bind together by hydrogen bonds, and thus the plant fibers constituting the paper stick together. In addition, examples of the other fibers include minerals, metals, and synthetic resins in the form of fibers. From the viewpoint of more firmly fixing the identification substance 38, paper formed of plant fibers (cellulose) is preferred.

The SAP is a polymer that can absorb and hold water up to several hundred times to several thousand times its own weight. As the SAP, polymers of acrylic acid can be used. The polymers of acrylic acid have a large number of carboxyl groups and therefore have high hydrophilicity, and form gels having high water absorbency when further crosslinked into fine structures and formed in the form of sodium salts.

Examples of other hydrophilic polymers can include cellulose derivatives such as hydroxypropylmethylcellulose (HPMC), carboxymethylcellulose sodium (CMC-Na), and hydroxyethylcellulose (HEC); polysaccharides such as alginic acid, hyaluronic acid, agarose, starch, dextran, and pullulan and derivatives thereof; homopolymers such as carboxyvinyl polymers, polyethylene oxide, poly(meth)acrylamide, and poly(meth)acrylic acid, copolymers of the homopolymers and polysaccharides or the like, and copolymers of monomers constituting the homopolymers and other monomers; proteins such as collagen and gelatin and derivatives thereof; and polysaccharides and mucopolysaccharides such as glycosaminoglycans such as heparin, hyaluronic acid, chondroitin sulfate, dermatan sulfate, dextran sulfate, keratan sulfate, and heparan sulfate, chitin, and chitosan.

Further, hydrophilic polymers such as 1-vinyl-2-pyrrolidinone, 2-methyl propenoate ester, monomethacryloyloxyethyl phthalate, ammonium sulfatoethyl methacrylate, N-vinylpyrrolidone, N,N-dimethylacrylamide, and 2-(methacryloyloxyethyl)-2-(trimethylammonioethyl) phosphate may be used.

The above illustrated hydrophilic polymers may be used singly, or two or more types may be used in combination.

As the polymerization initiator, a known radical polymerization accelerator can be timely selected and used. Preferably, one having water solubility or water dispersibility and uniformly contained in the entire system is preferably used. Specifically, as the polymerization initiator, in addition to water-soluble peroxides, for example, potassium peroxodisulfate and ammonium peroxodisulfate, and water-soluble azo compounds, for example, VA-044, V-50, and V-501 (all manufactured by Wako Pure Chemical Industries, Ltd.), a mixture of $Fe^{2+}$ and hydrogen peroxide, and the like can be used.

As the crosslinking agent, N,N'-methylenebisacrylamide, ethylene glycol dimethacrylate, vinyl methacrylate, and the like can be used.

(2-2) Manufacturing Method

The identification portion 12B shown in FIG. 4 can be manufactured by the following procedure. First, 0.15 g of 4-vinylphenylboronic acid, 1.0 g of hydroxyethyl methacrylate, 0.5 g of N-(3-dimethylaminopropyl)methacrylamide, and 0.05 g of N,N'-methylenebisacrylamide as a crosslinking agent are provided, and 6.0 g of a 6.7% by weight sodium acrylate aqueous solution (pH 7.3) is adjusted to a total amount of 10 g with ultrapure water. They are mixed for dissolution in a container 18. Then, 25 µl of tetramethylethylenediamine and 7.5 mg of potassium peroxodisulfate as polymerization initiators are added to initiate polymerization. This state is held under a nitrogen atmosphere at room temperature for 2 hours. After the completion of the polymerization reaction, the solution comprising the produced copolymer is immersed in ultrapure water to remove the unreacted components, and thus the receptor 20B in which the identification substance 38 and the inhibitor 41 are copolymerized can be obtained. The identification portion 12B can be manufactured in this manner.

(2-3) Action and Effect

In the identification portion 12B formed as described above, the hydrophilic polymer, the inhibitor, has water molecules adsorbed therearound and has high solvent affinity. Therefore, glucose comes into contact with the hydrophilic polymer via the water molecules and therefore dissolves in the solvent without being adsorbed. Thus, the glucose contained in the sample binds to the phenylboronic acid in the receptor 20B, and thus a negative charge is produced, and the electrode 16 is charged with the negative charge. Therefore, in the identification portion 12B, an effect similar to that in the above first embodiment can be obtained.

In addition, in the receptor 20B according to this embodiment, the identification substance 38 binds to the inhibitor 41 formed of the hydrophilic polymer to form a copolymer. The hydrophilic polymer has water molecules adsorbed therearound and has high solvent affinity. Therefore, a protein comes into contact with the hydrophilic polymer via the water molecules and therefore dissolves in the solvent without being adsorbed. Thus, in identification portion 12B, the protein contained in the sample is prevented from binding to the identification substance 38 or attaching to the surface of the electrode 16 by the inhibitor 41, and therefore the measurement sensitivity can be further improved. Therefore, the biosensor can more reliably measure glucose concentration based on a sample noninvasively collected from a human body.

The inhibitor 41 may have a molecular template having the same structure as the molecular structure of glucose (not shown). The inhibitor 41 having the molecular template can selectively take in the glucose contained in the sample, and therefore the measurement sensitivity can be further improved.

(2-4) Modification

An identification portion 12C according to a modification of the second embodiment will be described with reference to FIG. 5 in which like numerals refer to parts corresponding to those in FIG. 4. The identification portion 12C according to this embodiment is different from the identification portion according to the above second embodiment in that an identification substance 38 is supported on a support 44.

A receptor 20C comprises the support 44, the identification substance 38 supported on the support 44, and an inhibitor 41 and is formed of a copolymer in which the identification substance 38 binds to the inhibitor 41.

For the support 44, conductive particles and nonconductive particles can be used. For the conductive particles, metal particles, for example, particles of Au, Pt, Ag, Cu, and the like, and nonmetal particles, for example, particles of Indium Tin Oxide (ITO), conductive polymers, and the like, can be used. In addition, for the nonconductive particles, for example, particles of $SiO_2$ and the like can be used. For example, by introducing a thiol group (—SH) or a disulfide group (—S—S—) into phenylboronic acid as an identification substance to form a derivative of a thiol or a disulfide, the phenylboronic acid can be supported on the surfaces of Au particles.

A procedure for manufacturing the receptor 20C will be described. Specifically, first, 9 ml of a gold nanocolloidal solution (5 nm diameter,) and 1 ml of a 10 mM 4-mercaptophenylboronic acid (manufactured by Sigma-Aldrich Corporation)/ethanol solution are mixed, and allowed to stand at 25° C. for 24 hours to form a phenylboronic acid-gold nanoparticle solution. Next, 1.0 g of hydroxyethyl methacrylate (HEMA), 5 g of the above phenylboronic acid-gold nanoparticle solution, 0.5 g of N-3-(dimethylamino)propylmethacrylamide, 3 g of a 6.7% by weight sodium acrylate aqueous solution (pH 7.3), and 0.05 g of N,N'-methylenebisacrylamide are mixed, and adjusted with ultrapure water so that the total amount is 10 g. Then, 5 mg of potassium peroxodisulfate and 5 µl of tetramethylenediamine as polymerization initiators are added to initiate polymerization. This state is held under a nitrogen atmosphere at room temperature for 2 hours. After the completion of the polymerization reaction, the solution comprising the produced copolymer is immersed in ultrapure water to remove the unreacted components, and thus the receptor 20C in which the identification substance 38 and the inhibitor 41 are copolymerized can be obtained. The identification portion 12C can be manufactured in this manner.

As shown in FIG. 6, some of the identification substance 38 supported on the support 44 binds to the inhibitor 41 (numeral 45 in the figure) to form a copolymer. The remaining identification substance 38 supported on the support 44 binds to glucose 40 contained in a sample. The glucose 40 contained in the sample binds to the identification substance 38, and thus a negative charge is produced, and an electrode 16 is charged with the negative charge. Therefore, an effect similar to that in the above first embodiment can be obtained.

In addition, in the identification portion 12C according to this modification, the identification substance 38 binds to the inhibitor 41 formed of a hydrophilic polymer to form a copolymer, and therefore the protein contained in the sample can be prevented from binding to the identification substance 38 or attaching to the surface of the electrode 16. Therefore, also in the identification portion 12C according to this modification, an effect similar to that in the above second embodiment can be obtained.

Further, in the identification portion 12C according to this modification, the identification substance 38 is supported on the support 44, and therefore the identification substance 38 can also be easily fixed particularly to paper.

(Relationship between Glucose Concentration and Gate Voltage Change)

Next, a biosensor comprising the identification portion shown in FIG. 4 was manufactured by the procedure shown in the above "(2-2) Manufacturing Method." For a sample, Phosphate buffered saline (PBS) having a pH of 7.4 and comprising 4 g/L albumin was provided, and glucose was added thereto stepwise in the range of 50 µM to 1.25 mM to increase glucose concentration stepwise. The results are shown in FIG. 7.

From FIG. 7, the correlation coefficient was 0.9959, and the slope was 6.438, and it was confirmed that a linear relationship was seen between the logarithm of glucose concentration and gate voltage change. From the above results, it was confirmed that by using a copolymer in which an identification substance bound to an inhibitor formed of a hydrophilic polymer, an increase in negative charge due to a protein was inhibited.

Next, a biosensor comprising the identification portion shown in FIG. 5 was manufactured by the procedure shown in the above "(2-4) Modification." For the inhibitor in this case, hydroxyethyl methacrylate was used. For a sample, Phosphate buffered saline (PBS) having a pH of 7.4 and comprising 4 g/L albumin was provided, and glucose was added thereto stepwise in the range of 50 µM to 1.25 mM to increase glucose concentration stepwise. The results are shown in FIG. 8.

From FIG. 8, the correlation coefficient was 0.9959, and the slope was 6.438, and substantially the same results as FIG. 7 were obtained. From the above results, it was confirmed that even if a copolymer in which an identification substance supported on a support bound to an inhibitor formed of a hydrophilic polymer was used, an increase in negative charge due to a protein was inhibited.

Further, a biosensor in which the inhibitor was changed to cellulose in the identification portion shown in FIG. 5 was manufactured by the procedure shown below. Specifically, first, 9 ml of a gold nanocolloidal solution (5 nm diameter) and 1 ml of a 10 mM 4-mercaptophenylboronic acid (manufactured by Sigma-Aldrich Corporation)/ethanol solution were mixed, and allowed to stand at 25° C. for 24 hours to form a phenylboronic acid-gold nanoparticle solution. Next, 500 µl of the above phenylboronic acid-gold nanoparticle solution was dropped on Kimwipes (registered trademark) cut to a length of 40 mm and a width of 10 mm, and dried at 60° C. The Kimwipes (registered trademark) after the drying was adhered to a gate electrode portion using a polydimethylsiloxane solution (manufactured by Dow Corning Toray Co., Ltd.) to obtain a molecule identification member in which paper and phenylboronic acid-gold nanoparticles were mixed.

For a sample, Phosphate buffered saline (PBS) having a pH of 7.4 and comprising 4 g/L albumin was provided, and glucose was added thereto stepwise in the range of 10 µM to 2 mM to increase glucose concentration stepwise. The results are shown in FIG. 9.

From FIG. 9, the correlation coefficient was 0.9846, and the slope was 20.123, and it was confirmed that a linear relationship was seen between the logarithm of glucose concentration and gate voltage change. From the above results, it was confirmed that even when an identification substance supported on a support was fixed to an inhibitor formed of cellulose, an increase in negative charge due to a protein was inhibited.

In addition, a biosensor in which a molecular template was formed in the inhibitor in the identification portion shown in FIG. 4 was manufactured by the procedure shown below. First, 0.2 g of hydroxyethyl methacrylate (HEMA), 0.1 g of N-3-(dimethylamino)propylmethacrylamide, 0.01 g of vinylphenylboronic acid, 0.02 g of N,N'-methylenebisacrylamide, 300 µl of 6.7% by weight sodium acrylate (pH 7.3), and 0.009 g of glucose were adjusted to a total amount of 1 g with a 100 mM sodium phosphate buffer (pH 10.0) and dissolved, and then 10 µl of potassium peroxodisulfate (50 mg/ml, manufactured by Wako Pure. Chemical Industries, Ltd.) and 2 µl of tetramethylenediamine (manufactured by TOKYO CHEMICAL INDUSTRY CO., LTD.) as polymerization initiators were added to make a monomer solution.

Next, 15 µl of the monomer solution was dropped on an electrode 5 mm square formed of gold, covered with a PET (polyethyleneterephtalate) film, and subjected to a polymerization reaction under a nitrogen atmosphere at room temperature for 12 hours to make a hydrogel on the electrode. After the completion of the polymerization reaction, the gate electrode was immersed in a 0.1 M hydrochloric acid/methanol solution overnight to remove the monomer components and glucose to form a receptor in which an identification substance and an inhibitor were copolymerized. In this manner, a biosensor according to the embodiment in which the electrode surface was covered with a receptor was made.

As a comparison, the same receptor as the above was formed in an area 5 mm square on an electrode 10 mm square formed of gold to make a biosensor in which part of the electrode was exposed.

1500 µl of a 100 mM sodium phosphate buffer (pH 9.0) was dropped on the receptor of the biosensor made, and a gate voltage of 1 V and a source-drain current of 700 µA were made constant by a FET real time measurement apparatus. In this state, a change in gate electrode surface potential when 15 µl of 1 M glucose and 15 µl of a 100 mg/ml albumin solution were added to the receptor was measured.

The results are shown in FIG. 10. In FIG. 10, the vertical axis shows gate voltage (V), and the horizontal axis shows time (seconds). In this figure, the solid line is the results of the biosensor according to the above embodiment, and the broken line is the results of the biosensor made as a comparison.

From this figure, in the biosensor according to the embodiment, the gate surface potential when 10 mM glucose is added changes in the negative direction. From this, it was confirmed that in the biosensor according to the embodiment, a response to glucose was obtained. In addition, in the biosensor according to the embodiment, the gate surface potential did not change even if albumin was added. From this, it was confirmed that in the biosensor according to the embodiment, the inhibitor inhibited an increase in negative charge due to the protein. On the other hand, in the biosensor made as a comparison, the gate surface potential changed when albumin was added. This is considered to be due to the fact that the albumin binds to the electrode.

3. Third Embodiment

An identification portion 12D according to a third embodiment will be described with reference to FIG. 11 in which like numerals refer to parts corresponding to those in FIG. 2. The identification portion 12D according to this embodiment is different from the identification portion according to the above first embodiment in that an inhibitor is formed on an identification substance 38 in the form of a layer.

A receptor 20D comprises a thin film 46 formed of the identification substance 38, and an inhibitor layer 47 formed on the thin film 46 and formed of an inhibitor.

The thin film 46 is an SAM formed by the adsorption of one end of the identification substance 38 on one side surface of an electrode 16. The inhibitor layer 47 is formed of a hydrophilic polymer comprising a hydrogel, a SAP, or the like. In the case of this embodiment, the inhibitor layer 47 is formed of hydroxyethyl methacrylate.

The thin film 46 can be made by forming a self-assembled monolayer as in the procedure shown in "(1-2) Manufacturing Method" in the above first embodiment. Specifically, a gold substrate is immersed in a 1 mM 4-mercaptophenylboronic acid (manufactured by Sigma-Aldrich Corporation)/ ethanol solution at 25° C. for 24 hours to make a self-assembled monolayer.

The inhibitor layer 47 is made by the following procedure. 1.0 g of hydroxyethyl methacrylate (HEMA), 0.5 g of N-3-(dimethylamino)propylmethacrylamide, 6 g of a 6.7%; by weight sodium acrylate aqueous solution (pH 7.3), and 0.05 g of N,N'-methylenebisacrylamide are mixed, and adjusted with ultrapure water so that the total amount is 10 g. Then, 5 mg of potassium peroxodisulfate and 5 µl of tetramethylenediamine as polymerization initiators are added to initiate polymerization. This state is held under a nitrogen atmosphere at room temperature for 2 hours. After the completion of the polymerization reaction, the solution comprising the produced copolymer is immersed in ultrapure water to remove the unreacted components, and thus the inhibitor layer 47 can be manufactured.

Finally, the inhibitor layer 47 formed of hydroxyethyl methacrylate is laid on the thin film 46 formed of the identification substance 38, and thus the identification portion 12D can be manufactured.

In the identification portion 12D formed as described above, the hydrophilic polymer, the inhibitor, has water molecules adsorbed therearound and has high solvent affinity. Therefore, glucose 40 comes into contact with the hydrophilic polymer via the water molecules and therefore dissolves in the solvent without being adsorbed. Thus, the glucose 40 binds to the identification substance 38, and a negative charge is produced, and the electrode 16 is charged with the negative charge. Therefore, in the identification portion 12D, an effect similar to that in the above first embodiment can be obtained.

In addition, in the receptor 20D according to this embodiment, the thin film 46 of the identification substance 38 formed on the electrode 16 is covered with the inhibitor layer 47. The hydrophilic polymer forming the inhibitor layer 47 has water molecules adsorbed therearound and has high solvent affinity. Therefore, a protein comes into contact with the hydrophilic polymer via the water molecules and therefore dissolves in the solvent without being adsorbed. Thus, in identification portion 12D, a protein 42 contained in a sample is prevented from binding to the identification substance 38 or attaching to the surface of the electrode 16 by the inhibitor layer 47, and therefore the measurement sensitivity can be further improved. Therefore, the biosensor can more reliably measure glucose concentration based on a sample noninvasively collected from a human body.

(Modification)

In the above third embodiment, a case where the number of inhibitor layers is one has been described, but the present invention is not limited to this, and two or more inhibitor layers formed of hydrophilic polymers having different molecular weights may be formed.

(Relationship between Glucose Concentration and Gate Voltage Change)

Next, a biosensor comprising the identification portion shown in FIG. 11 was manufactured by the above-described procedure. For a sample, Phosphate buffered saline (PBS) having a pH of 7.4 and comprising 4 g/L albumin was provided, and glucose was added thereto stepwise in the range of 10 µM to 2 mM to increase glucose concentration stepwise. The results are shown in FIG. 12.

From FIG. 12, the correlation coefficient was 0.9877, and the slope was 25.94, and it was confirmed that a linear relationship was seen between the logarithm of glucose concentration and gate voltage change. From the above results, it was confirmed that by laying in the form of a layer an inhibitor formed of a hydrophilic polymer on a thin film formed of an identification substance, an increase in negative charge due to a protein was inhibited.

4. Modifications

The present invention is not limited to the above embodiments, and appropriate changes can be made within the spirit of the present invention. For example, in the case of the above embodiments, a case where the detection portion is a FET has been described, but the present invention is not limited to this, and light-receiving elements such as photodiodes and photomultipliers, thermistors, Quartz Crystal Microbalances (QCMs), elements utilizing surface plasmon resonance, and the like can also be used.

In addition, a case where the identification portion and the detection portion are electrically connected by wiring has been described, but the present invention is not limited to this, and the identification portion and the detection portion may be integrally formed. In other words, the electrode may be directly formed on the gate insulating film of the FET as the detection portion.

REFERENCE SIGNS LIST 10 biosensor
12A, 12B, 12C, 12D identification portion
14 FET (detection portion)
16 electrode
28 gate insulating film
30 metal electrode
31 wiring
38 identification substance
39, 41 inhibitor
40 glucose (substance to be detected)
42 protein (substance not to be detected)
44 support
46 thin film
47 inhibitor layer

The invention claimed is:
1. A biosensor comprising
an identification substance that binds to a substance to be detected, and
an electrode, wherein
the biosensor comprises an inhibitor that inhibits a substance not to be detected from attaching to at least one of the identification substance and the electrode;

the identification substance is in contact with the electrode;
the inhibitor is formed of a polymer compound having a longer molecular chain than the identification substance;
a self-assembled monolayer is formed on a surface of the electrode from the identification substance and the inhibitor; and
the biosensor detects a change in a charge density of the electrode caused by binding of the substance to be detected to the identification substance,
wherein the electrode is connected to a gate insulating film of a field effect transistor, and
wherein the electrode is disposed away from the field effect transistor and electrically connected to a metal electrode provided on the gate insulating film via wiring.

2. The biosensor according to claim 1, wherein the substance to be detected is glucose.

3. The biosensor according to claim 1, wherein the identification substance is phenylboronic acid.

4. A biosensor comprising
an identification substance that binds to a substance to be detected, and
an electrode, wherein
the biosensor comprises an inhibitor that inhibits a substance not to be detected from attaching to at least one of the identification substance and the electrode;
the biosensor comprises a thin film provided on the electrode and formed of the identification substance, and
one or two or more inhibitor layers formed on the thin film and comprising the inhibitor; and
the biosensor detects a change in a charge density of the electrode caused by binding of the substance to be detected to the identification substance
wherein at least one of the inhibitor layers is formed of homopolymers and/or copolymers of polyhydroxyethyl methacrylate (Poly-HEMA), polyvinylpyrrolidone (PVP), polyvinyl alcohol (PVA), 2,3-dihydroxypropyl methacrylate, glycerol methacrylate (GMA), N-vinyl-2-pyrrolidone (NVP), methyl methacrylate (MMA), or any combination thereof.

5. The biosensor according to claim 4, wherein the electrode is connected to a gate insulating film of a field effect transistor.

6. The biosensor according to claim 5, wherein the electrode is disposed away from the field effect transistor and electrically connected to a metal electrode provided on the gate insulating film via wiring.

7. The biosensor according to claim 4, wherein the identification substance is phenylboronic acid.

8. A biosensor comprising an identification substance that binds to a substance to be detected, and
an electrode, wherein
the biosensor comprises an inhibitor that inhibits a substance not to be detected from attaching to at least one of the identification substance and the electrode;
the identification substance is supported on a conductive or nonconductive particles support and bound to the inhibitor, wherein the inhibitor comprises a hydrophilic polymer and molecular templates are formed in the inhibitor, wherein the molecular templates have a structure complementary to a molecular structure of the substance to be detected, wherein the entire surface area of the electrode facing a sample is covered with the inhibitor, wherein the hydrophilic polymer is a hydrogel, paper, or a Superabsorbent Polymer (SAP), wherein the conductive or nonconductive particles support comprises particles of gold (Au), platinum (Pt), silver (Ag), indium tin oxide (ITO), $SiO_2$, or any combination thereof; and
the biosensor detects a change in a charge density of the electrode caused by binding of the substance to be detected to the identification substance.

9. The biosensor according to claim 8, wherein the electrode is connected to a gate insulating film of a field effect transistor.

10. The biosensor according to claim 9, wherein the electrode is disposed away from the field effect transistor and electrically connected to a metal electrode provided on the gate insulating film via wiring.

11. The biosensor according to claim 8, wherein the identification substance is phenylboronic acid.

* * * * *

UNITED STATES PATENT AND TRADEMARK OFFICE
CERTIFICATE OF CORRECTION

PATENT NO. : 11,156,581 B2
APPLICATION NO. : 14/907934
DATED : October 26, 2021
INVENTOR(S) : Sakata et al.

Page 1 of 1

It is certified that error appears in the above-identified patent and that said Letters Patent is hereby corrected as shown below:

On the Title Page

(56) References Cited, OTHER PUBLICATIONS, Column 2:
Please correct "Reinhoudtetal." to read -- Reinhoudt et al. --

(56) References Cited, OTHER PUBLICATIONS, Page 2, Column 2, Line 3:
Please correct "Moussyetal." to read -- Moussy et al. --

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*